United States Patent [19]

Souda et al.

[11] Patent Number: 5,708,013
[45] Date of Patent: Jan. 13, 1998

[54] PYRIDINE DERIVATIVE AND THERAPEUTIC AGENT FOR ULCER COMPRISING THE SAME

[75] Inventors: Shigeru Souda, Ushiku; Norihiro Ueda, Tsukuba; Shuhei Miyazawa, Toride; Katsuya Tagami, Niihari-gun; Seiichiro Nomoto, Ushiku; Makoto Okita; Naoyuki Shimomura, both of Tsukuba; Toshihiko Kaneko, Ushiku; Masatoshi Fujimoto, Tsukuba; Manabu Murakami, Tsukuba; Kiyoshi Oketani, Tsukuba; Hideaki Fujisaki, Tsukuba; Hisashi Shibata, Tsuchiura; Tsuneo Wakabayashi, Mito, all of Japan

[73] Assignee: Eisai Co., Ltd., Japan

[21] Appl. No.: 524,109

[22] Filed: Aug. 21, 1995

Related U.S. Application Data

[63] Continuation of Ser. No. 224,184, Apr. 7, 1994, abandoned, which is a continuation of Ser. No. 93,146, Jul. 19, 1993, abandoned, which is a continuation of Ser. No. 950,753, Sep. 24, 1992, abandoned, which is a continuation of Ser. No. 831,774, Feb. 10, 1992, abandoned, which is a continuation of Ser. No. 668,699, Mar. 7, 1991, abandoned, which is a continuation of Ser. No. 207,626, Jun. 16, 1988, abandoned.

[30] Foreign Application Priority Data

Jun. 19, 1987 [JP] Japan ................... 62-150986

[51] Int. Cl.⁶ ................... A61K 31/44; C07D 401/12
[52] U.S. Cl. ................... 514/338; 546/273.7
[58] Field of Search ................... 546/273.7; 514/338

[56] References Cited

U.S. PATENT DOCUMENTS

| | | | |
|---|---|---|---|
| 4,255,431 | 3/1981 | Junggren et al. | 514/338 |
| 4,337,257 | 6/1982 | Junggren et al. | 424/263 |
| 4,508,905 | 4/1985 | Junggren et al. | 546/271 |
| 4,555,518 | 11/1985 | Rainer | 514/338 |
| 4,686,230 | 8/1987 | Rainer et al. | 514/338 |
| 4,746,667 | 5/1988 | Carlsson et al. | 546/271 |

FOREIGN PATENT DOCUMENTS

| | | |
|---|---|---|
| 0167943 | 1/1986 | European Pat. Off. |
| 0173644 | 3/1986 | European Pat. Off. |
| 8602646 | 5/1986 | WIPO |

Primary Examiner—Joseph McKane
Attorney, Agent, or Firm—Nixon & Vanderhye

[57] ABSTRACT

A pyridine compound having the formula is disclosed and useful to treat the peptic ulcer.

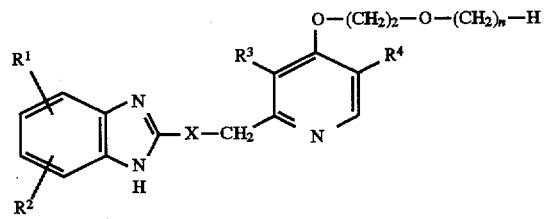

wherein $R^1$ and $R^2$ which may be the same or different are each a hydrogen atom, a lower alkyl group, a lower alkoxy group, a halogenated lower alkyl group, or a halogen atom, $R^3$ and $R^4$ which may be the same or different are each a hydrogen atom or a lower alkyl group, X is a group represented by the formula —S—, a group represented by the formula

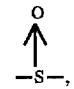

or a group represented by the formula

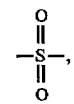

and n is an integer of 1 to 6, provided that $R^3$ and $R^4$ are not simultaneously hydrogen atoms when n is 1.

9 Claims, No Drawings

PYRIDINE DERIVATIVE AND THERAPEUTIC AGENT FOR ULCER COMPRISING THE SAME

This is a Rule 62 File Wrapper Continuation of application Ser. No. 08/224,184, filed Apr. 7, 1994, now abandoned, which is a continuation of Ser. No. 08/093,146, filed Jul. 19, 1993, now abandoned, which is a continuation of Ser. No. 07/950,753, filed Sep. 24, 1992, now abandoned which is a continuation of Ser. No. 07/831,744, filed Feb. 10, 1992, now abandoned, which is a continuation of Ser. No. 07/668,699, filed Mar. 7, 1991, now abandoned, which in turn is a continuation of Ser. No. 07/207,626, filed Jun. 16, 1988, now abandoned.

The present invention relates to a pyridine derivative having an excellent antiulcerative activity.

[Prior Art]

A generally accepted theory about the occurrence of peptic ulcers, such as gastric or duodenal ulcer, is that the upset of a balance between attacking factors, such as an acid or pepsin, and protective factors, such as mucous resistance, mucus, blood flow, or control of duodenum causes self-digestion which in turn brings about an ulcer.

In principle, peptic ulcer is internally treated and various medical treatments have been attempted. Examples of antiulcerative agents which are currently most popular include cimetidine and ranitidine due to histamine-$H_2$ receptor antagonism. However, these drugs are reported to cause side effects, such as an antiandrogenic action or a metabolic enzymatic activity inhibitory action upon liver.

Under these circumstances, in recent years, it was suggested that inhibitors for an enzyme called ATPase which is specifically present in the wall of the stomach can function as an excellent acid secretion inhibitor. Among them, a known compound which is currently drawing particular attention is omeprazole which is a benzimidazole derivative represented by the following structural formula (see Japanese Patent Laid-Open No. 141783/1979):

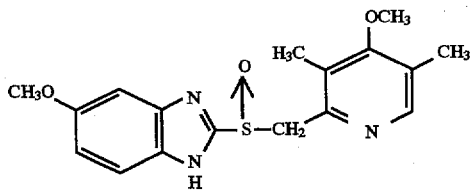

Thereafter, various benzimidazole compounds having an antiulcerative activity were proposed. Examples of such compounds include those described in Japanese Patent Laid-Open No. 18277/1984 and No. 24589/1986.

In view of the above situation, the present inventors have continued extensive and intensive searches and studies with a view to finding out a compound having an antiulcerative activity and safety superior to those of known benzimidazole compounds such as omeprazole.

(SUMMARY OF THE INVENTION)

The object compound of the present invention is a pyridine derivative and a pharmacologically acceptable salt thereof represented by the following general formula:

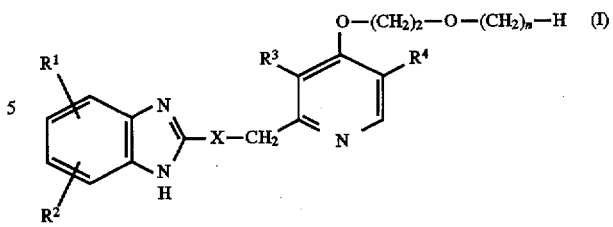

wherein $R^1$ and $R^2$ which may be the same or different are each a hydrogen atom, a lower alkyl group, a lower alkoxy group, a halogenated lower alkyl group, or a halogen atom, $R^3$ and $R^4$ which may be the same or different are each a hydrogen atom or a lower alkyl group, X is a group represented by the formula —S—, a group represented by the formula

or a group represented by the formula

and n is an integer of 1 to 6, provided that $R^3$ and $R^4$ are not simultaneously hydrogen atoms when n is 1.

The present inventors have continued searches and studies in order to attain the above-described object. As a result, it has been found out that a pyridine derivative or a pharmacologically acceptable salt thereof represented by the above general formula (I) exhibits superior safety and antiulcerative activity, which led to the completion of the present invention.

Therefore, an object of the present invention is to provide a novel pyridine derivative and a pharmacologically acceptable salt thereof which can effectively function as a therapeutic agent for peptic ulcer. Another object of the present invention is to provide a process for preparing said compound or pharmacologically acceptable salt thereof. A further object of the present invention is to provide a pharmaceutical containing said compound or pharmaceutically acceptable salt thereof as an effective ingredient.

The present inventors noted the 4-position of a pyridine ring as represented by the above general formula (I) and completed the present invention. A substituent at the 4-position is an alkoxyalkoxy group, i.e., [—O—$(CH_2)_2$—O—$(CH_2)_n$—H]. In this group, the number of carbon atoms of the first alkoxy group is 1 to 6 (i.e., n is an integer of 1 to 6), while the number of carbon atoms of the second alkoxy group is always 2.

The compound of the present invention has not been disclosed so far and therefore is a novel compound. Specifically, for example, the above-described Japanese Patent Laid-Open Nos. 18277/1984 and 49910/1979 each disclose a compound having a methoxyethoxy group at the 4-position of the pyridine ring. However, specifically disclosed compounds are only ① those having hydrogen atoms attached to both the 3- and 5-positions of the pyridine ring, ② those in which the phenyl ring of the benzimidazole ring is substituted with a cycloalkyl group, and ③ those which have hydrogen atoms attached to both the 3- and 5-positions of the pyridine ring and in which the 4-, 5-, and 6-positions of the benzimidazole ring are each substituted with a methyl group and therefore are different from the compound of the present invention.

Further, Japanese Patent Laid-Open No. 24589/1986 specifically discloses only a compound is which the 4-position of the pyridine ring is substituted with a benzyloxyalkoxy group and, therefore, this compound is also different from the compound of the present invention.

The term "lower alkyl group" used in the above definition of $R^1$, $R^2$, $R^3$, and $R^4$ of the compound (I) of the present invention is intended to mean a straight-chain or branched alkyl group having 1 to 6 carbon atoms, and examples thereof include methyl, ethyl, n-propyl, n-butyl, isopropyl, isobutyl, 1-methylpropyl, tert-butyl, n-pentyl, 1-ethylpropyl, isoamyl, and n-hexyl groups. The most preferable examples thereof include methyl and ethyl groups.

The term "lower alkoxy group" used in the difinition of $R^1$ and $R^2$ is intended to mean a group derived from the above-described lower alkyl group having 1 to 6 carbon atoms. The most preferable examples thereof include methoxy and ethoxy groups.

The term "halogen atom" is intended to mean chlorine, bromine, iodine, and fluorine.

Further, the term "halogenated lower alkyl group" is intended to mean a group comprising the above-described lower alkyl group in which hydrogen atom(s) is (are) substituted with one or more of the above-described halogen atoms. The most preferable examples thereof include a trifluoromethyl group.

A pyridine compound of the invention is preferred to have a lower alkyl for R3 and R4 and —SO— for X in the formula and then have a lower alkyl for one of R3 and R4 and —SO— for X in the formula.

Examples of the pharmacologically acceptable salt include salts of inorganic acids, such as hydrochloride, hydrobromide, sulfate, and phosphate; those of organic acids, such as acetate, maleate, tartrate, methanesulfonate, benzenesulfonate, and toluenesulfonate; and those of amino acids such as arginine, aspartic acid, and glutamic acid.

Further, certain compounds are in the form of metallic salts such as Na, K, Ca, or Mg salts, and these metallic salts are also within the scope of the pharmacologically acceptable salt.

Specifically, for example, the pharmacologically acceptable salt include the following one:

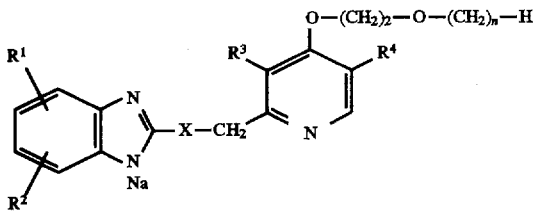

Further, the compound of the present invention may form a hydrate or may be composed of stereoisomers. These are, of course, within the scope of the present invention.

Processes

The compound of the present invention can be prepared by various processes. Representative processes will now be described.

Process A

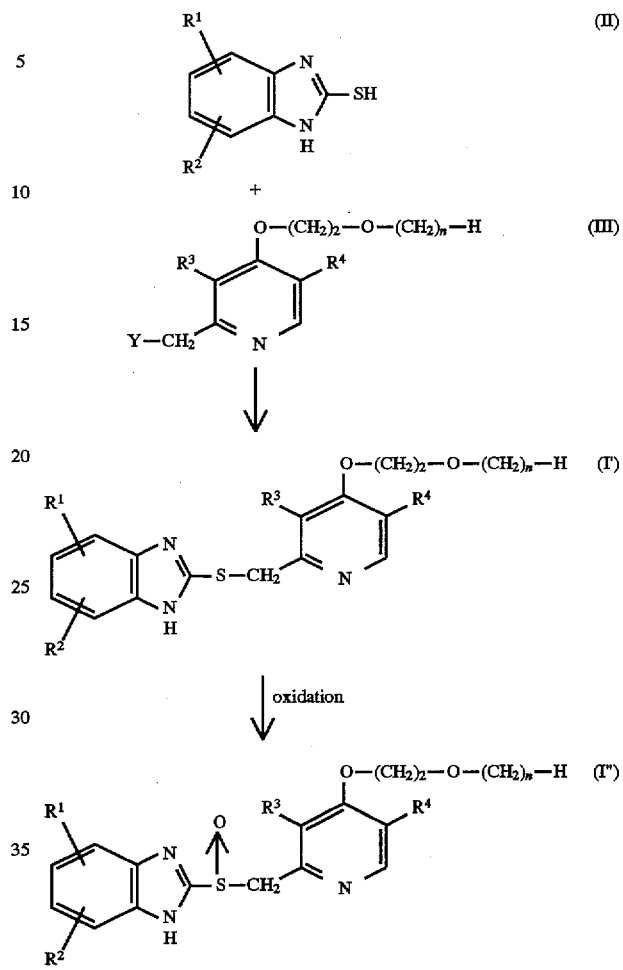

wherein $R^1$, $R^2$, $R^3$, $R^4$, and n are as defined above and Y is a halogen atom or one of various sulfonyloxy groups.

A compound (I') which is one of the object substances can be prepared by reacting a compound represented by the general formula (II) with a halogen compound or a sulfonate compound represented by the general formula (III).

In the definition of Y, the term "halogen atom" is intended to mean, e.g., chlorine, bromine, and iodine, and the term "various sulfonyloxy groups" is intended to mean, e.g., alkylsulfonyloxy groups such as a methylsulfonyloxy or ethylsulfonyloxy group, and aromatic sulfonyloxy groups such as a benzenesulfonyloxy or tosyloxy group.

This reaction provides good results when conducted in the presence of a deoxidizer. Examples of the deoxidizer include carbonates and bicarbonates of alkali metals such as potassium carbonate, sodium carbonate, and sodium bicarbonate; alkali hydroxides such as sodium hydroxide and potassium hydroxide; and organic amines such as pyridine and triethylamine. Examples of the solvent used in the reaction include alcohols such as methyl and ethyl alcohols, tetrahydrofuran, dioxane, dimethylformamide, and a mixture thereof with water.

The reaction temperature ranges from −40° C. to the boiling point of the solvent, preferably about 0° to 60° C.

A sulfinyl derivative (I") which is one of the object substances can easily be prepared by further subjecting the compound (I') thus obtained to oxidation.

The oxidation can be conducted, e.g., by making use of an oxidizing agent, such as hydrogen peroxide, peracetic acid, m-chloroperbenzoic acid, sodium hypochlorite, or sodium bromite, according to a customary method. The solvent used in the reaction is usually selected from among dichloromethane, chloroform, benzene, toluene, methanol, ethanol, etc. The reaction temperature ranges from about −70° C. to the boiling point of the solvent, preferably from −60° to 25° C.

When the object substance is a sulfone compound, i.e., a compound represented by the [formula (I) wherein X is a group represented by the formula

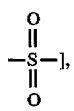

it can be prepared by, e.g., the following process:

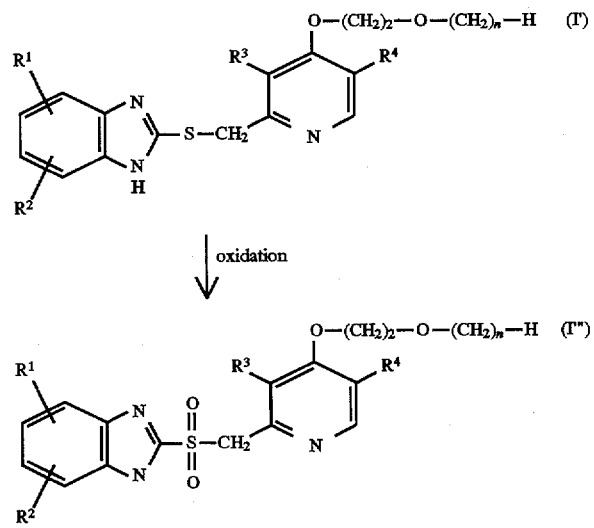

wherein $R^1$, $R^2$, $R^3$, $R^4$, and n are as defined above.

Specifically, a sulfone compound represented by the general formula (I''') which is one of the object substances can be prepared by oxidizing a thio ether derivative represented by the general formula (I') which is also one of the object substances.

More precisely, the sulfone compound (I''') which is one of the object substances can be prepared by a process which comprises dissolving the compound (I') in a solvent selected from among aromatic hydrocarbons such as benzene, toluene, and xylene, halogenated hydrocarbons such as dichloromethane, chloroform, and carbon tetrachloride, water, alcohols such as methanol and ethanol, ethyl acetate, acetone, and acetic acid, and adding at least 2 equivalents of an oxidizing agent, such as hydrogen peroxide, peracetic acid, m-chloroperacetic acid, sodium hypochlorite, or sodium m-periodate, to the resulting solution while cooling with ice or at room temperature, followed by reaction.

The sulfone compound (I''') can be prepared also by another process which comprises dissolving the sulfoxide compound (I'') prepared by the above-described process in a solvent, such as chloroform, and adding an oxidizing agent, such as m-chloroperbenzoic acid, to the resulting solution, followed by reaction.

Process B

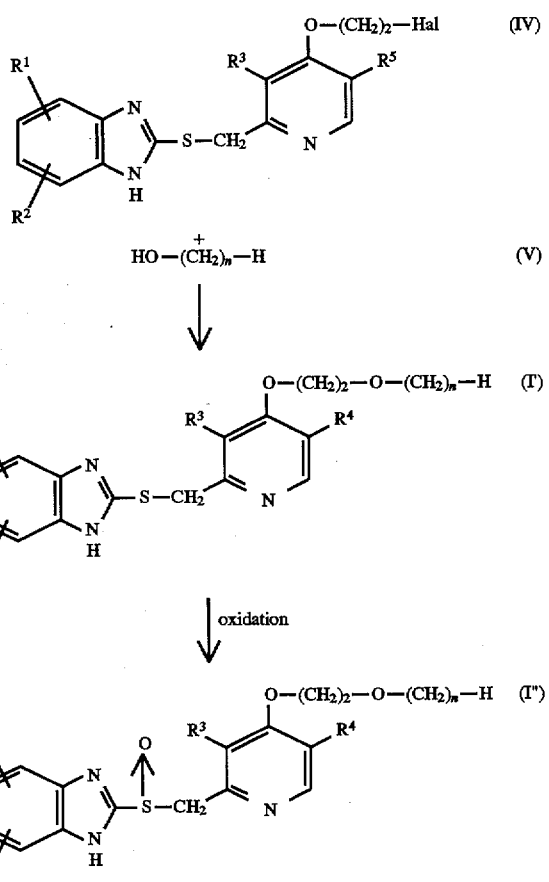

wherein $R^1$, $R^2$, $R^3$, $R^4$, and n are as defined above and Hal is a halogen atom.

Specifically, the object substance represented by the general formula (I') can be prepared by reacting a halogen compound represented by the general formula (IV) with an alcohol represented by the general formula (V). With respect to this reaction as well, it is preferred that the reaction be conducted in the presence of a deoxidizer. Examples of the deoxidizer include carbonates and bicarbonates of alkali metals such as potassium carbonate and sodium carbonate, alkali hydroxides such as sodium hydroxide and potassium hydroxide, and triethylamine. Examples of the solvent used in the reaction include ethers such as tetrahydrofuran and dioxane, ketones such as acetone and methyl ethyl ketone, solvents of benzene series such as benzene, toluene, and xylene, acetonitrile, dimethylformamide, dimethyl sulfoxide, and hexamethylphosphoric triamide. The reaction is conducted while cooling the reaction system with ice or at a temperature up to the boiling point of the solvent.

As described above with respect to the Process A, the compound (I') thus obtained which is one of the object substances can be oxidized with a suitable oxidizing agent to prepare a sulfinyl derivative represented by the general formula (I'').

Process for preparing starting material

[1] A compound represented by the general formula (III) which is used as a starting material in the Process A can be prepared by, e.g., the following process:

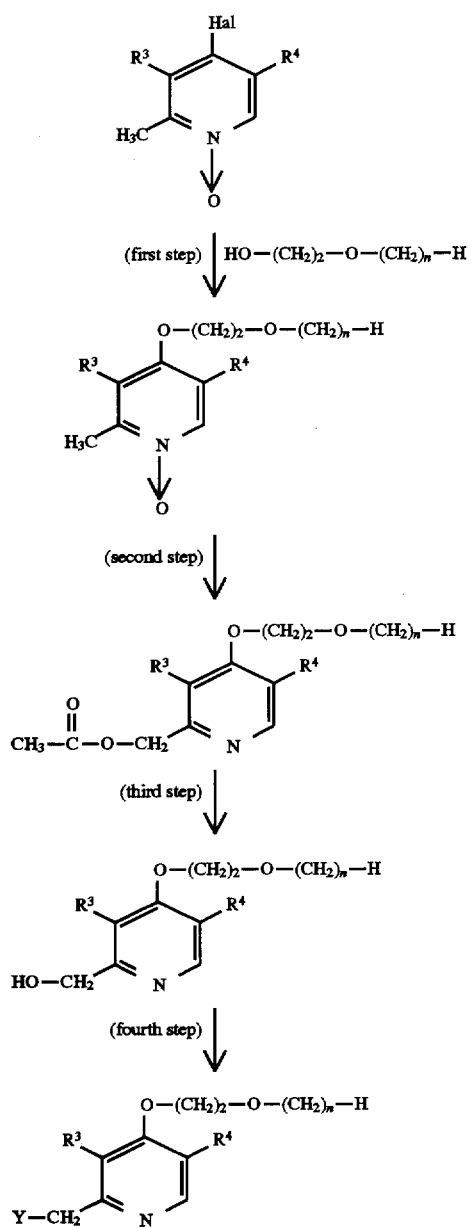

wherein Y, n, $R^3$, and $R^4$ are as defined above and Hal is a halogen atom.

First step

An alkoxy derivative represented by the general formula (VIII) can be prepared by reacting 4-halogenopyridine oxide derivative (VI), such as 4-chloro-2,3-dimethylpyridine 1-oxide, with an alcohol derivative represented by the general formula (VII) in the presence of a base.

Examples of the base include alkali metal hydrides such as sodium hydride and potassium hydride, alkali metals such as metallic sodium, sodium alcoholates such as sodium methoxide, and alkali hydroxides such as sodium hydroxide and potassium hydroxide. This reaction is conducted in the absence or presence of a solvent selected from among, e.g., ethers such as tetrahydrofuran and dioxane, ketones such as acetone and methyl ethyl ketone, solvents of benzene series such as benzene, toluene, and xylene, acetonitrile, dimethylformamide, dimethyl sulfoxide, and hexamethylphosphoric triamide.

The reaction is suitably conducted while cooling the reaction system with ice or at a temperature up to the boiling point of the solvent.

Second step

An alkoxy derivative represented by the general formula (VIII) prepared in the first step is heated at about 60° to 100° C. in acetic anhydride to prepare an acetoxymethylpyridine derivative represented by the general formula (IX).

Third Step

In this step, the acetoxymethylpyridine derivative (IX) prepared in the second step is hydrolyzed to prepare a 2-hydroxymethylpyridine derivative represented by the general formula (X).

The hydrolysis is usually conducted with an alkali.

Fourth step

A 2-halogenomethylpyridine represented by the general formula (III) can be prepared by halogenating the 2-hydroxymethylpyridine derivative (X) prepared in the third step with, e.g., a chlorinating agent such as thionyl chloride. In this case, e.g., chloroform, dichloromethane, or the like is used as a solvent. Further, a sulfonyloxy derivative represented by the general formula (III) can be prepared by sulfonylating the 2-hydroxymethylpyridine derivative (X) with, e.g., an active sulfonyl chloride such as methanesulfonyl chloride. Examples of the solvent used in this reaction include chloroform, dichloromethane, ether, tetrahydrofuran, pyridine, and benzene.

[2] In the above process, the compound represented by the general formula (VIII) can be prepared also by the following process:

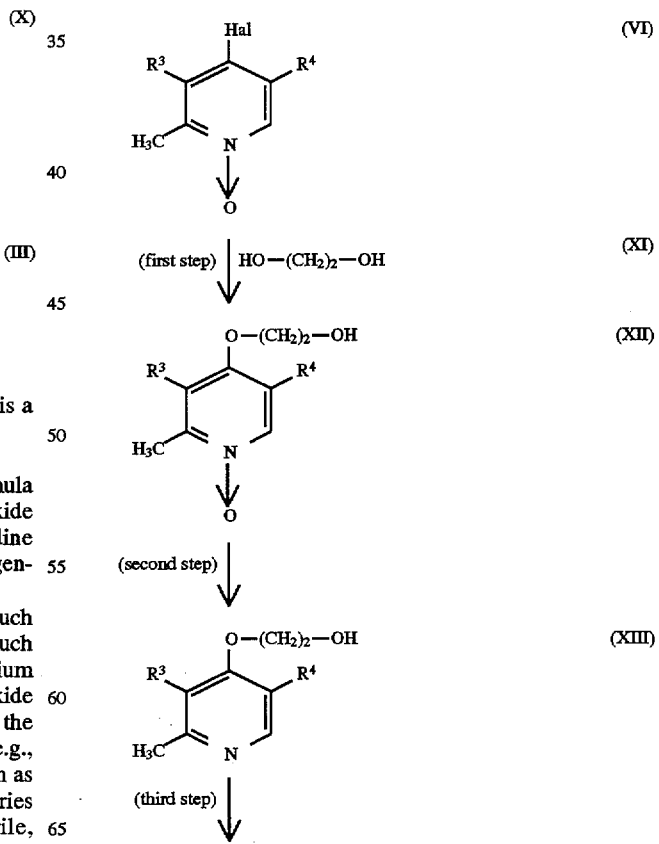

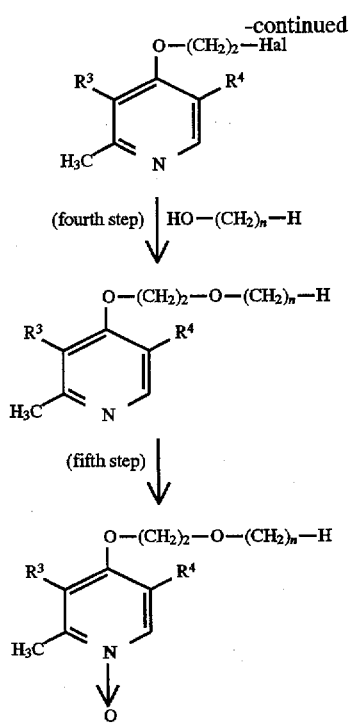

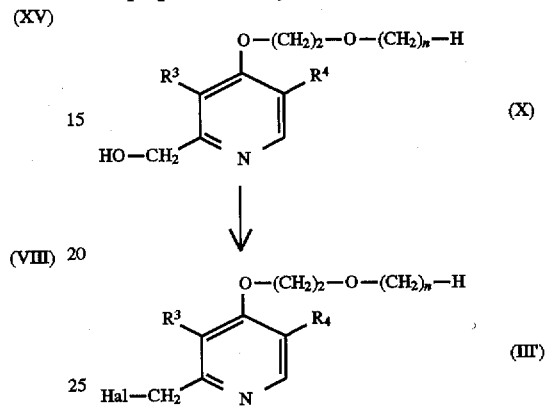

wherein $R^3$, $R^4$, and n are as defined above and Hal is a halogen atom.

First Step

A compound represented by the general formula (VI) wherein Hal is a halogen atom, such as a chlorine atom, is subjected to a condensation reaction with a compound represented by the general formula (XI) according to an ordinary method to prepare a compound represented by the general formula (XII).

This reaction is preferably conducted in the presence of a base, e.g., an alkali metal hydride such as sodium hydride or potassium hydride, an alkali metal such as metallic sodium, and an alkali hydroxide such as sodium hydroxide or potassium hydroxide.

Further, this reaction is conducted in the absence or presence of a solvent, e.g., an ether such as tetrahydrofuran or dioxane, a ketone such as acetone or methyl ethyl ketone, a solvent of benzene series such as benzene, toluene, or xylene, acetonitrile, dimethylformamide, dimethyl sulfoxide, or hexamethylphosphoric triamide. The reaction is suitably conducted while cooling the reaction system with ice or at a temperature up to the boiling point of the solvent used.

Second Step

This step comprises reducing the above formed alkoxy derivative (XII) to prepare the compound (XIII). Specifically, the reductant (XIII) can be prepared by, e.g., hydrogenation of the alkoxy derivative (XII) in an acetic anhydride/acetic acid mixture in the presence of a catalyst comprising 10% palladium-carbon.

Third Step

A 2-halogenoethyl derivative represented by the general formula (XIV) can be prepared by halogenating the above formed compound (XIII) with, e.g., a halogenating agent such as thionyl chloride. Examples of the solvent used in this reaction include chloroform and dichloromethane.

Fourth step

A compound represented by the general formula (XV) can be prepared by reacting the above formed compound (XIV) with an alcohol represented by the formula (V). As with the reaction in the process B, this reaction also provides good results when conducted in the presence of a deoxidizer.

Fifth step

An N-oxide compound (VIII) can be prepared by oxidizing the above formed compound (XV) with, e.g., an oxidizing agent such as hydrogen peroxide, peracetic acid, or m-chloroperbenzoic acid.

[3] In the Process A, the compound represented by the general formula (III) which is used as a starting material can be prepared also by the following process:

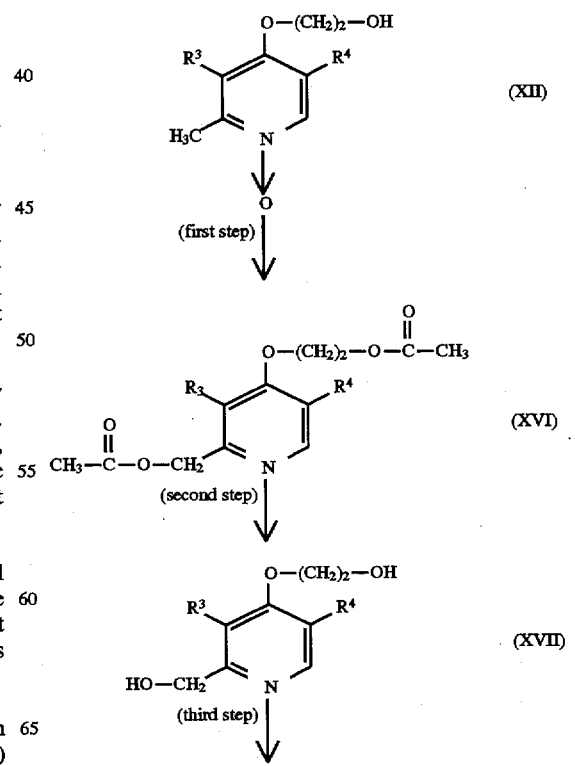

wherein $R^3$, $R^4$, n, and Hal are as described above.

A halogenomethylpyridine derivative represented by the general formula (III') can be prepared by halogenating a compound represented by the general formula (X) with, e.g., a chlorinating agent, such as thionyl chloride, at room temperature to 0° C. Examples of the solvent used in this reaction include chloroform and dichloromethane.

[4] The compound (IV) which is a starting material in the Process B can be prepared by, e.g., the following process:

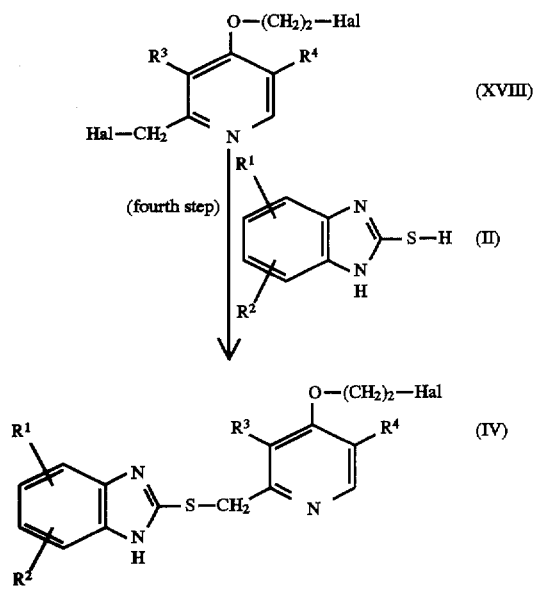

wherein Hal is a halogen atom and the other symbols are as defined above.

First Step

In this step, a compound represented by the general formula (XII) is converted into an acetylated compound (XVI). Specifically, the compound is acetylated with, e.g., acetic anhydride or acetyl chloride.

Second Step

The acetylated compound thus formed is hydrolyzed in the presence of an acid or a base to prepare a diol compound (XVII).

Third Step

The diol compound (XVII) is halogenated with, e.g., a halogenating agent, such as thionyl chloride, to prepare a dihalogenated compound represented by the general formula (XVIII). Examples of the solvent used in this reaction include chloroform and dichloromethane.

Fourth step

In this step, the dihalogenated compound (XVIII) thus formed is reacted with a compound represented by the general formula (II) to prepare a sulfide derivative represented by the general formula (IV).

It is preferred that this reaction be conducted in the presence of a deoxidizer selected from among carbonates and bicarbonates of alkali metals such as potassium carbonate, sodium carbonate, and sodium bicarbonate and alkali hydroxides such as sodium hydroxide and potassium hydroxide. Examples of the solvent used in this reaction include alcohols, such as ethanol and methanol, tetrahydrofuran, dioxane, dimethylformamide, dimethyl sulfoxide, and a mixture thereof with water. The reaction temperature ranges from 0° C. to the boiling point of the solvent used, preferably from about 40° to 60° C.

[5] The compound (IV) used as a starting material in the Process B can be prepared also by the following process:

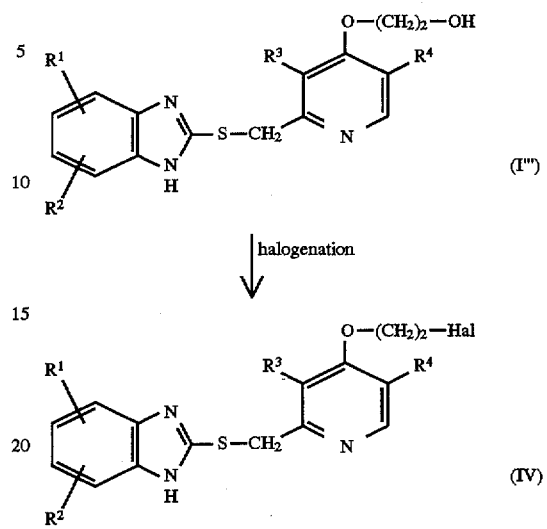

wherein Hal is a halogen atom and the other symbols are as defined above.

Specifically, a compound (IV) which is a halogenated compound can be prepared by halogenating the compound (I''') according to an ordinary method. The halogenation is conducted with, e.g., a chlorinating agent such as thionyl chloride. Preferred examples of the solvent used in this reaction include chloroform and dichloromethane. A reaction temperature ranging from room temperature to 80° C. provides good results.

The effect of the present invention will now be described in more detail with reference to the following examples of pharmacological experiment.

Examples of pharmacological experiment $H^+$—$K^+$ATPase activity inhibition (1) Preparation of $H^+$—$K^+$ATPase:

$H^+$—$K^+$ATPase was prepared from a gland portion of the gastric fundus of the gastiric mucosa of a fresh pig by the modification of a method of Saccomani et al., Biochem. and Biophys. Acta, 464, 313(1977).

(2) Determination of $H^+$—$K^+$ATPase activity:

The compound of the present invention was incubated in various concentrations together with $H^+$—$K^+$ATPase and 10 µg/ml of protein in 40 mM of Tris-HCl having a pH value of 7.40 at 37° C. for 30 min. 15 mM of KCl was added thereto. 10 min after the addition, an ATPase reaction was initiated by addition of 3 mM of $MgCl_2$ and ATP. 10 min after the initiation of the reaction, the amount of the released inorganic phosphoric acid was measured according to the method of Yoda and Hokin, Biochem. Biophys. Res., Com., 40, 880(1970).

The test compound was dissolved in methanol prior to use.

The inhibitory effect was determined as follows. The measured value of the test compound was subtracted from the measured value of the control group to determine the difference in the measured values therebetween. The inhibitory effect was calculated as the percentage of the difference relative to the measured value of the control group. In the Table, the inhibitory effect was expressed in terms of $IC_{50}$.

(3) The results are shown in Table 1.

In Table 1, Bu stands for a butyl group, Et an ethyl group, and Me a methyl group.

TABLE 1

| No. | Compound | IC$_{50}$(M) |
| --- | --- | --- |
| 1 | | $1.8 \times 10^{-6}$ |
| 2 | | $1.8 \times 10^{-6}$ |
| 3 | | $1.1 \times 10^{-6}$ |
| 4 | | $2.2 \times 10^{-6}$ |
| 5 | | $3.0 \times 10^{-6}$ |
| 6 | | $2.8 \times 10^{-6}$ |
| 7 | | $1.5 \times 10^{-6}$ |

TABLE 1-continued

| No. | Compound | IC$_{50}$(M) |
|---|---|---|
| 8 | Me-benzimidazole-S(O)Na-CH$_2$-pyridine(CH$_3$)-O-(CH$_2$)$_2$-OEt | 2.6 × 10$^{-6}$ |
| 9 | MeO-benzimidazole-S(O)Na-CH$_2$-pyridine(CH$_3$)-O-(CH$_2$)$_2$-OEt | 3.4 × 10$^{-6}$ |
| 10 | benzimidazole-S(O)Na-CH$_2$-pyridine(CH$_3$)-O-(CH$_2$)$_2$-OMe | 3.3 × 10$^{-6}$ |
| 11 | CF$_3$-benzimidazole-S(O)Na-CH$_2$-pyridine(CH$_3$)-O-(CH$_2$)$_2$-OMe | 1.7 × 10$^{-6}$ |
| 12 | MeO-benzimidazole-S(O)Na-CH$_2$-pyridine(CH$_3$)-O-(CH$_2$)$_2$-OMe | 5.6 × 10$^{-6}$ |
| 13 | Omeprazole | 1.1 × 10$^{-5}$ |

It is apparent from the above experimental examples that the compound of the present invention exhibits a strong $H^+$—$K^+$ATPase activity inhibitory action. The compound of the present invention is predominant over other benzimidazole compounds with respect to the $H^+$—$K^+$ATPase activity inhibitory action, and the action is far superior to that of omeprazole (see Japanese Patent Laid-Open No. 14783/1979) which is presently drawing the keenest attention.

Further, the compound of the present invention is a novel compound which is not disclosed in any of Japanese Patent Laid-Open Nos. 18277/1984 and 24589/1986 referred to in the item of "Prior Art" and further characterized in that it can function as a therapeutic agent for peptic ulcer. These documents do never suggest that feature. Specifically, the feature of the compound of the present invention resides in that the compound of the present invention is superior in the ability of restoring the secretion of gastric juice to a normal state to that of the conventional compounds such as omeprazole. This is a property required of current therapeutic agents for peptic ulcer. Therefore, the present invention is invaluable.

Further, the compound of the present invention has excellent safety, which renders it useful as an excellent gastric juice secretion inhibitor. This in turn renders the compound of the present invention useful as a therapeutic and preventive agent for peptic ulcer of human beings and animals.

When the compound of the present invention is used as a therapeutic and preventive agent for peptic ulcer, it may be orally administered in the form of powders, granules, capsules, medicated syrups, etc. or parenterally administered in the form of suppositories, parental preparations, external preparations or dripping preparations. The does of the compound of the present invention will remarkably vary depending upon the symptom, age, kind of the ulcer, etc. However, the compound may normally be administered in a dose of about 0.01 to 200 mg/kg, preferably 0.05 to 50 mg, more preferably 0.1 to 10 mg/kg per day in one to several portions.

Pharmaceutical preparations are prepared from the compound of the present invention by making use of a commonly accepted carrier for pharmaceutical preparations according to an ordinary method.

Specifically, when a solid preparation for oral administration is prepared, the effective ingredient is blended with a vehicle and, if necessary, a binder, a disintegrator, a lubricant, a colorant, a corrigent, etc., followed by preparation of tablets, coated tablets, granules, powders, and capsules.

Examples of the vehicle include lactose, corn starch, sucrose, glucose, sorbitol, crystalline cellulose, and silicon dioxide. Examples of the binder include polyvinyl alcohol, polyvinyl ether, ethylcellulose, methylcellulose, acacia, tragacanth, gelatin, shellac, hydroxypropylcellulose, hydroxypropylstarch, and polyvinylpyrrolidone. Examples of the disintegrator include starch, agar, gelatin powder, crystalline cellulose, calcium carbonate, sodium bicarbonate, calcium citrate, dextrin, and pectin. Examples of the lubricant include magnesium stearate, talc, polyethylene glycol, silica, and hydrogenated vegetable oil. Any colorant of which the addition to pharmaceuticals is officially allowed can be used as the colorant. Examples of the corrigent include cacao powder, menthol, aromatic powder, mentha powder, borneol, and powdered cinnamon bark. It is a matter of course that a sugar coating, a gelatin coating and, if necessary, suitable other coatings may be applied on these tablets and granules.

When parenteral preparations are prepared, a pH adjustor, a buffering agent, a stabilizer, a solubilizing agent, etc. are added to the effective ingredient, followed by preparation of parenteral preparations for subcutaneous injection, intramuscular injection, and intravenous injection according to an ordinary method.

[EXAMPLES]

Examples of the present invention will now be described. It is needless to say that the invention of the present invention is not limited to these only.

In the examples, the term "Preparation Example" is intended to mean the preparation of a starting material used in the preparation of the object substance of the present invention.

Preparation Example 1

4-{2-Ethoxy)ethoxy}-2,3-dimethylpyridine 1-oxide

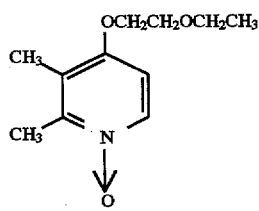

6.3 g of 4-chloro-2,3-dimethylpyridine 1-oxide and 7.2 g of 2-ethoxyethanol were dissolved in 100 ml of dimethyl sulfoxide. 3.2 g of sodium hydride (60%) was added thereto in portions at room temperature. The resulting mixture was stirred at room temperature for 2 hr and then at 40° C. for 1 hr. Dimethyl sulfoxide was distilled off, followed by purification by silica gel column chromatography, thereby preparing 7.1 g of 4-{(2-ethoxy)ethoxy}-2,3-dimethylpyridine 1-oxide.

$^1$H-NMR (CDCl$_3$) δ; 1.23(t, J=7.0 Hz, 3H), 2.2(s, 3H), 2.53(s, 3H), 3.59(q, J=7.0 Hz, 2H), 3.80(t, J=4.6 Hz, 2H), 4.16(t, J=4.6 Hz, 2H), 6.42(d, J=7.5 Hz, 1H), 8.39(d, J=7.5 Hz, 1H)

Preparation Example 2

4{(2-Ethoxy)ethoxy}-2-hydroxymethyl-3-methylpyridine

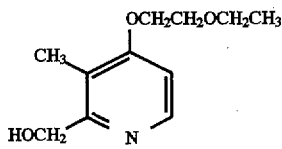

7.0 g of 4-{(2-ethoxy)ethoxy}-2,3-dimethylpyridine 1-oxide was dissolved in 50 ml of acetic anhydride. The resulting solution was stirred at 90° C. for 2 hr. Acetic anhydride was then distilled off. 60 ml of ethanol and 4.0 g of sodium hydroxide were added to the residue, followed by stirring at 40° C. for 1 hr. The reaction mixture was filtered, and ethanol was distilled off from the filtrate. Water was added to the residue, followed by extraction with chloroform. The extract was dried over magnesium sulfate, and chloroform was distilled off, thereby preparing 6.1 g of 4-{(2-ethoxy)ethoxy}-2-hydroxymethyl-3-methylpyridine.

$^1$H-NMR (CDCl$_3$) δ; 1.24(t, J=7.0 Hz, 3H), 2.06(s, 3H), 3.61(q, J=7.0 Hz, 2H), 3.81(t, J=4.8 Hz, 2H), 4.18(t, J=4.8 Hz, 2H), 4.64(s, 2H), 6.71(d, J=6.1 Hz, 1H), 8.28(d, J=8.1 Hz, 1H)

Preparation Example 3

2-Chloromethyl-4-{(2-ethoxy)ethoxy}-3-methylpyridine

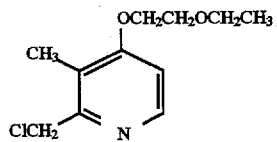

1.5 g of 4-{(2-ethoxy)ethoxy}-2-hydroxymethyl-3-methylpyridine was dissolved in 20 ml of dichloromethane. 2.5 g of thionyl chloride was dropwise added thereto at 0° C. Thereafter, the resulting mixture was stirred at room temperature for 2 hr. After the completion of the reaction, dichloromethane and excess thionyl chloride were distilled off. 30 ml of a saturated aqueous sodium bicarbonate solution was added to the residue, followed by extraction with dichloromethane. The extract was dried over magnesium sulfate, and dichloroethane was distilled off, thereby preparing 1.55 g of 2-chloromethyl-4-{(2-ethoxy)ethoxy}-3-methylpyridine.

$^1$H-NMR (CDCl$_3$) δ; 1.24(t, J=7.0 Hz, 3H), 2.29(s, 3H), 3.61(q, J=7.0 Hz, 2H), 3.81(t, J=4.8 Hz, 2H), 4.15(t, J=4.8 Hz, 2H), 4,68(s, 2H), 6.72(d, J=5.7 Hz, 1H), 8.28(d, J=5.7 Hz, 1H)

Example 1

2-[4-{(2-Ethoxy) ethoxy}-3-methylpyridin-2-yl]methylthio-1H-benzimidazole

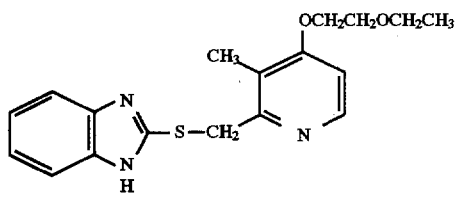

40 ml of ethanol was added to a mixture of 1.6 g of 2-chloromethyl-4-{(2-ethoxy)ethoxy}-3-methylpyridine with 0.73 g of 2-mercaptobenzimidazole and 0.6 g of sodium hydroxide. The mixture was then stirred at 40° C. for 2 hr. The reaction mixture was concentrated as such and purified by silica gel column chromatography, thereby preparing 1.55 g of 2-[4-{(2-ethoxy)ethoxy}-3-methylpyridin-2-yl]-methylthio-1H-benzimidazole.

$^1$H-NMR(CDCl$_3$) δ; 1.22(t, J=7.0 Hz, 3H), 2.25(s, 3H), 3.59(q, J=7.0 Hz, 2H), 3.79(t, J=4.9 Hz, 2H), 4.15(t, J=4.9 Hz, 2H), 4.39(s, 2H), 6.71(d, J=5.7 Hz, 1H), 6.95~7.24(m, 2H), 7.30~7.58 (m, 2H), 8.30(d, J=5.7 Hz, 1H)

Examples 2 to 4

The same procedures as those described above were repeated to prepare the following compounds.

(Example 2)

2-[4-{(2-Ethoxy)ethoxy}-3-methylpyridin-2-yl]methylthio-5-methoxy-1H-benzimidazole

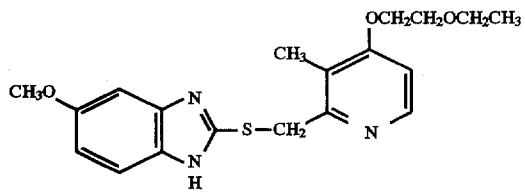

$^1$H-NMR (CDCl$_3$) δ; 1.23 (t, J=7.0 Hz, 3H), 2.25(s, 3H), 3.59(q, J=7.0 Hz, 2H), 3.82(s, 3H), 3.7~3.9(2H), 4.16(t, J=5.2 Hz, 2H), 4.37(s, 2H). 6.6~7.3(m, 4H), 8.31(d, J=5.7 Hz, 1H)

(Example 3)

2-[4-{(2-Ethoxy)ethoxy}-3-methylpyridin-2-yl]methylthio-5-methyl-1H-benzimidazole

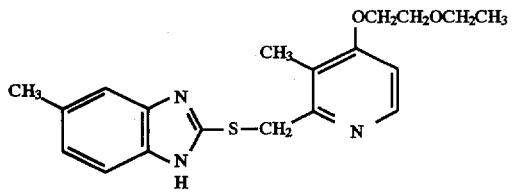

$^1$H-NMR (CDCl$_3$) δ; 1.23(t, J=7.1 Hz, 3H), 2.26(s, 3H), 2.43(s, 3H), 3.57(q, J=7.1 Hz, 2H) 3.70~3.86(m, 2H), 4.02~4.22(m, 2H), 4.32(s, 2H), 6.69(d, J=5.3 Hz, 1H), 6.82~7.44(m, 3H), 8.26(d, J=5.3 Hz, 1H)

(Example 4)

2-[4-{(2-Ethoxy)ethoxy}-3-methylpyridin-2-yl]methylthio-5-trifluoromethyl-1H-benzimidazole

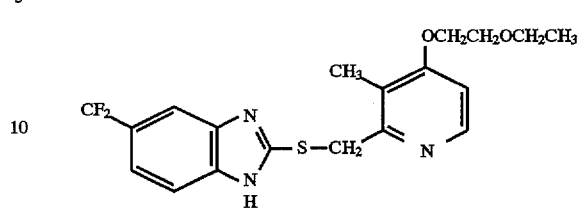

$^1$H-NMR (CDCl$_3$) δ; 1.23(t, J=7.2 Hz. 3H), 2.27(s, 3H), 3.57(q, J=7.2 Hz, 2H), 3.70~3.89(m, 2H), 4.07~4.23(m, 2H), 4.34(s, 3H), 6.72(d, J=6.3 Hz, 1H), 7.15~7.79(m, 3H), 8.27(d, J=6.3 Hz, 1H)

Example 5

2-[4-{(2-Ethoxy)ethoxy}-3-methylpyridin-2-yl]methylsulfinyl-1H-benzimidazole sodium salt

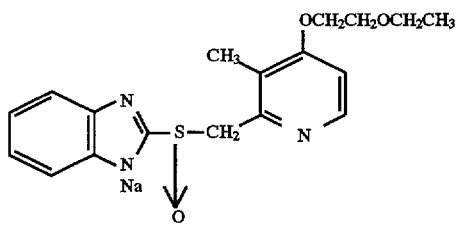

0.8 g of 2-[4-{(2-ethoxy)ethoxy}-3-methylpyridin-2-yl]methylthio-1H-benzimidazole was dissolved in 30 ml of dichloromethane. 0.45 g of m-chloroperbenzoic acid was added thereto at −65° C. 2 hr after the completion of the addition, 0.7 g of triethylamine was added thereto at −30° C., and 30 ml of an aqueous 1N sodium hydroxide solution was further added thereto, followed by stirring at room temperature for 30 min. The resulting phases were separated from each other. The water phase was washed twice with 20 ml of dichloromethane. An aqueous 2M ammonium acetate solution was added to the water phase to adjust a pH value to 11, followed by extraction with dichloromethane. The extract was dried over magnesium sulfate and filtered. The filtrate was concentrated and dried in vacuo. 20 ml of an aqueous 0.1N sodium hydroxide solution was added to the residue and water was distilled off, thereby preparing 0.71 g of the intended product.

$^1$H-NMR(DMSO-d$_5$) δ; 1.13(t, J=7.0 Hz, 3H) 2.16(s, 3H), 3.52(q, J=7.0 Hz, 1H), 3.67~3.80(m, 2H), 4.10~4.21(m, 2H), 4.6(ABq, J=12.7 Hz, Δv=18.5 Hz, 2H), 6.80~7.05(m, 3H), 7.38~7.60(m, 2H), 8.26(d, J=5.3 Hz, 1H)

Examples 6 to 8

The same procedures as those described above were repeated to prepare the following compounds.

(Example 6)

2-[4-{(2-Ethoxy)ethoxy}-3-methylpyridin-2-yl]methylsulfinyl-5-methoxy-1H-benzimidazole sodium salt

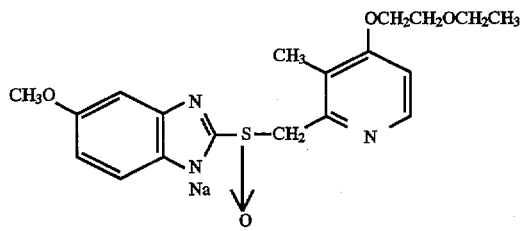

$^1$H-NMR (DMSO-d$_6$) δ: 1.13(t, J=7.0 Hz, 3H), 2.15(s, 3H), 3.52(q, J=7.0 Hz, 2H), 3.74(s, 3H), 3.6~3.80(2H), 4.01~4.22(m, 2H), 4.59(ABq, J=13.2 Hz, Δν=22.0 Hz, 2H), 6.61(dd, J=8.8 Hz, 2.2 Hz, 1H), 6.92(d, J=5.7 Hz, 1H), 7.01(d, J=2.2 Hz, 1H), 7.38(d, J=8.8 Hz, 1H), 8.25(d, J=5.7 Hz, 1H)

(Example 7)

2-[{4-(2-Ethoxy)ethoxy-3-methylpyridin-2-yl}-methylsulfinyl]-5-trifluoromethyl-1H-benzimidazole sodium salt

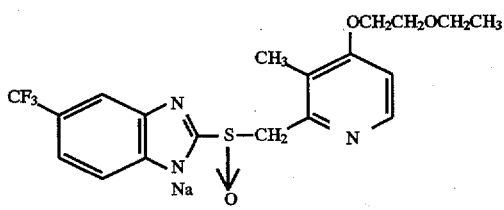

$^1$H-NMR (DMSO-d$_6$) δ; 1.12(t, J=7.03 Hz, 3H), 2.16(s, 3H), 3.52(q, J=7.03 Hz, 2H), 3.72(m, 2H), 4.12(m, 2H), 4.57(ABq, J=13.19 Hz, Δν=15.89 Hz, 2H), 6.93(d, J=5.71 Hz, 1H), 7.15(dd, J=7.35 Hz, 1.76 Hz, 1H), 7.6(d, J=7.35 Hz, 1H), 7.8(d, J=1.76 Hz, 1H), 8.28(d, J=5.71 Hz, 1H)

(Example 8)

2-[{4-(2-Ethoxy)ethoxy-3-methylpyridin-2-yl}methylsulfinyl]-5-methyl-1H-benzimidazole sodium salt

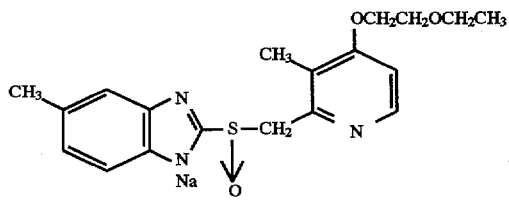

$^1$H-NMR (DMSO-d$_6$) δ; 1.13(t, J=7.03 Hz, 3H), 2.14(s, 3H), 2.39(s, 3H), 3.51(q, J=7.03 Hz, 2H), 3.71 (m, 2H), 4.15(m, 2H), 4.57(ABq, J=13.19 Hz, Δν=11.62 Hz, 2H), 6.86(m, 2H), 7.36(m, 2H), 8.22(d, J=5.72 Hz, 1H)

Example 9

2-[4-{(2-Butoxy)ethoxy}-3-methylpyridin-2-yl]methylthio-1H-benzimidazole

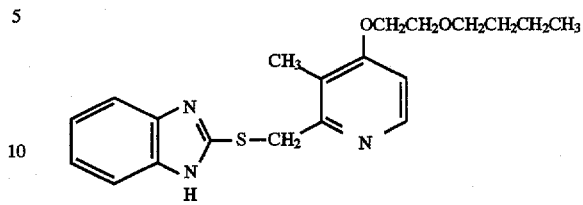

40 ml of ethanol was added to a mixture of 1.32 g of 4-{(2-butoxy)ethoxy}-2-chloromethyl-3-methylpyridine with 0.67 g of 2-mercaptobenzimidazole and 0.54 g of sodium hydroxide, followed by stirring at 40° C. for 2 hr. The reaction mixture was concentrated as such and purified by silica gel column chromatography, thereby preparing 1.66 g of the intended product.

$^1$H-NMR (CDCl$_3$) δ; 0.92(t, J=7.0 Hz, 3H), 1.10~1.80(m, 4H), 2.26(s, 3H), 3.53(t, J=6.3 Hz, 2H), 3.79(t, J=5.1 Hz, 2H), 4.17(t, J=5.1 Hz, 2H), 4.38(s, 2H), 6.74(d, J=5.7 Hz, 1H), 7.00~7.30(m, 2H), 7.30~7.60(m, 2H), 8.32(d, J=5.7 Hz, 1H)

Example 10 to 13

The same procedures as those described above were repeated to prepare the following compounds.

(Example 10)

2-[4-{(2-Butoxy)ethoxy}-3-methylpyridin-2-yl]methylthio-5-methoxy-1H-benzimidazole

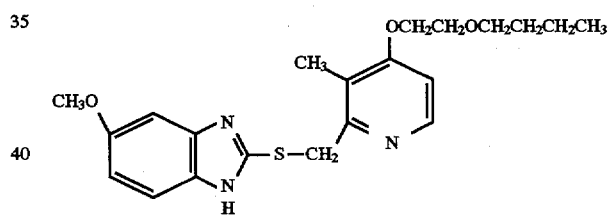

$^1$H-NMR (CDCl$_3$) δ; 0.91(t, J=6.6 Hz, 3H), 1.10~1.70(m, 4H), 2.24(s, 3H), 3.52(t, J=6.3 Hz, 2H). 3.82(s, 3H), 3.70~3.90(2H), 4.15(t, J=4.6 Hz, 2H), 4.37(s, 2H), 6.60~6.86(m, 2H), 7.02(d, J=2.1 Hz, 1H), 7.39(d, J=8.8 Hz, 1H), 8.31(d, J=5.7 Hz, 1H)

(Example 11)

2-[4-{(2-Butoxy)ethoxy}-3-methylpyridin-2-yl]methylthio-5-trifluoromethyl-1H-benzimidazole

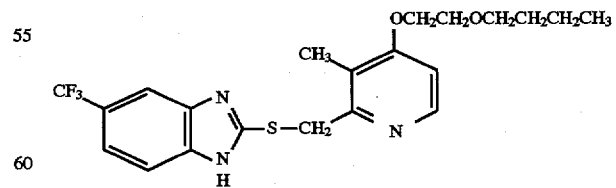

$^1$H-NMR (CDCl$_3$) δ; 0.91(t, J=6.6 Hz, 3H), 1.10~1.70(m, 4H), 2.27(s, 3H), 3.53(t, J=6.2 Hz, 2H), 3.80(t, J=4.6 Hz, 2H), 4.17(t, J=4.6 Hz, 2H), 4.40(s, 2H), 6.76(d, J=5.7 Hz, 1H), 7.40(d, J=8.4 Hz, 1H), 7.58(d, J=8.4 Hz, 1H), 7.79(s, 1H), 8.32(d, J=5.7 Hz, 1H)

(Example 12)

2-[4-{(2-Butoxy)ethoxy}-3-methylpyridin-2-yl]methylthio-5,6-dimethyl-1H-benzimidazole

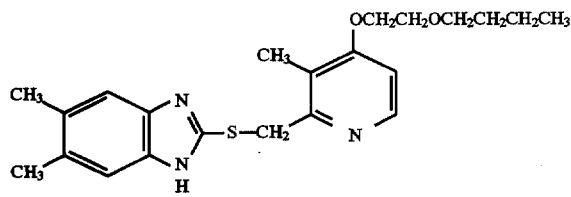

¹H-NMR (CDCl₃) δ; 0.91(t, J=1 Hz, 3H), 1.10~1.70(m, 4H), 2.25(s, 3H), 2.33(s, 6H), 3.53(t, J=6.4 Hz, 2H), 3.79(t, J=4.8 Hz, 2H), 4.15(t, J=4.8 Hz, 2H), 4.35(s, 2H), 6.72(d, J=5.7 Hz, 1H), 7.28(s, 2H), 8.3(d, J=5.7 Hz, 1H)

(Example 13)

2-[4-{(2-Butoxy)ethoxy}-3-methylpyridin-2-yl]methylthio-5-chloro-1H-benzimidazole

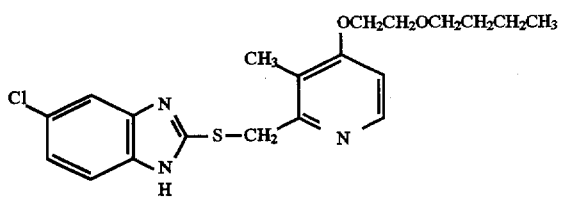

¹H-NMR (CDCl₃) δ; 0.91(t, J=6.6 Hz, 3H), 1.10~1.70(m, 4H), 2.25(s, 3H), 3.53(t, J=6.6 Hz, 2H), 3.79(t, J=4.6 Hz, 2H), 4.17(t, J=4.6 Hz, 2H), 4.36(s, 2H), 6.75(d, J=5.7 Hz, 1H), 7.11(d, J=8.3 Hz, 2.2 Hz, 1H), 7.2~7.5(m, 2H), 8.30(d, J=5.7 Hz, 1H)

Example 14

2-[4-{(2-Butoxy)ethoxy}-3-methylpyridin-2-yl]methylsulfinyl-1H-benzimidazole sodium salt

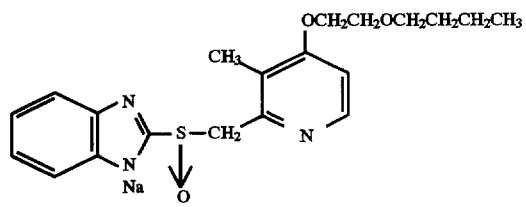

1.0 g of 2-[4-{(2-Butoxy)ethoxy}-methylpyridin-2-yl]methylthio-1H-benzimidazole was dissolved in 40 ml of dichloromethane. 0.55 g of m-chloroperbenzoic acid was added thereto at −65° C. 2 hr after the completion of the addition, 0.8 g of triethylamine was added thereto at −35° C., and 30 ml of an aqueous 1N sodium hydroxide solution was further added thereto, followed by stirring at room temperature for 30 min. The resulting phases were separated from each other. Thereafter, the water phase was washed twice with 20 ml of dichloromethane. An aqueous 2M ammonium acetate solution was added to the water phase to adjust a pH value to 11, followed by extraction with dichloromethane. The extract was concentrated by removing the solvent and dried in vacuo. 20 ml of an aqueous 0.1N sodium hydroxide solution was added to the residue and water was distilled off, thereby preparing 1.0 g of the intended product.

¹H-NMR(DMSO-d₆) δ; 0.87(t, J=6.2 Hz, 3H), 1.10~1.70 (m, 4H), 2.16(s,3H), 3.46(t, J=6.2 Hz, 2H), 3.5~3.8(m, 2H), 4.0~4.2(m, 2H), 4.63(ABq, J=13.2 Hz, Δν=19.8 Hz, 2H), 6.8~7.1(m, 3H), 7.3~7.6(m, 2H), 8.25(d, J=5.7 Hz, 1H)

Examples 15 to 18

The same procedures as those described above were repeated to prepare the following compounds.

(Example 15)

2-[4-{(2-Butoxy)ethoxy}-3-methylpyridin-2-yl]methylsulfinyl-5-methoxy-1H-benzimidazole sodium salt

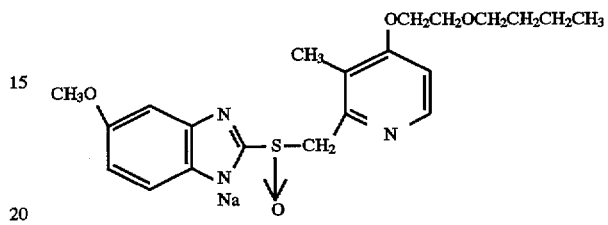

¹H-NMR (DMSO-d₆) δ; 0.87(t, J=5.7 Hz, 3H), 1.1~1.7 (m,4H), 2.15(s, 3H), 3.46(t, J=6.2 Hz, 2H), 3.72(s 3H) 3.55~3.75(m, 2H), 4.0~4.2(m, 2H), 4.53(ABq, J=12.7 Hz, Δν=19.9 Hz, 2H), 6.57(dd, J=5.7 Hz, 2.2 Hz, 1H), 6.91(d, J=5.7 Hz, 1H), 6.99(d, J=2.2 Hz, 1H), 7.34(d, J=8.3 Hz, 1H), 8.27(d, J=5.7 Hz, 1H)

(Example 16)

2-[4-{(2-Butoxy)ethoxy}-3-methylpyridin-2-yl]methylsulfinyl-5-trifluoromethyl-1H-benzimidazole sodium salt

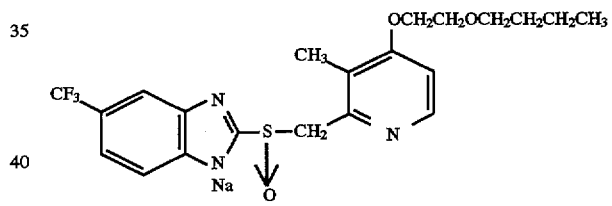

¹H-NMR (DMSO-d₆) δ; 0.87(t, J=5.7 Hz, 3H), 1.1~1.7 (m, 4H), 2.15(s, 3H), 3.46(t, J=6.1 Hz, 2H), 3.55~3.76(m, 2H), 3.98~4.20(m, 2H), 4.56(ABq, J=13.6 Hz, Δν=17.1 Hz, 2H), 6.92(d, J=5.7 Hz, 1H), 7.16(d, J=8.8 Hz, 1H), 7.62(d, J=8.8 Hz, 1H), 7.82(s, 1H), 8.28(d, J=5.7 Hz, 1H)

(Example 17)

2-[4-{(2-Butoxy)ethoxy}-3-methylpyridin-2-yl]methylsulfinyl-5,6-dimethyl-1H-benzimidazole sodium salt

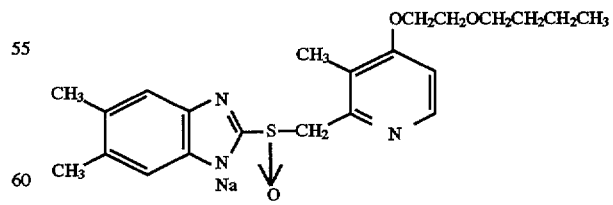

¹H-NMR (DMSO-d₆) δ; 0.87(t, J=6.6 Hz, 3H), 1.1~1.7( (m, 4H), 2.13(s, 3H), 2.27(s, 6H), 3.46(t, J=6.1 Hz, 2H), 3.55~3.75(m, 2H), 3.95~4.15(m, 2H), 4.52(ABq, J=13.2 Hz, Δν=18.6 Hz, 2H), 6.90(d, J=5.7 Hz, 1H), 7.25(s, 1H), 8.26(d, J=5.7 Hz, 1H)

(Example 18)

2-[4-{(2-Butoxy)ethoxy}-3-methylpyridin-2-yl]methylsulfinyl-5-chloro-1H-benzimidazole sodium salt

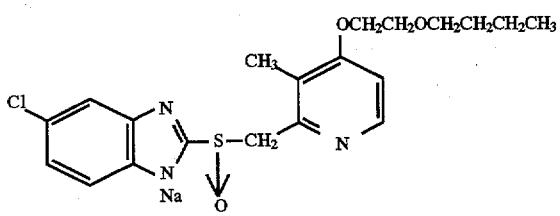

$^1$H-NMR (DMSO-d$_6$) δ; 0.88(t, J=6.5 Hz, 3H), 1.1~1.7 (m, 4H), 2.14(s, 3H), 3.46(t, J=5.7 Hz, 2H), 3.55~3.75(m, 2H), 3.95~4.20(m, 2H), 4.54(ABq, J=13.2 Hz, Δv=18.9 Hz, 2H), 6.7~6.9(m, 2H), 7.3~7.5(m, 2H), 8.27(d, J=5.3 Hz, 1H)

Example 19

2-[{4-(2-Butoxy)ethoxy-3-methylpyridin-2-yl}-methylthio]-1H-benzimidazole

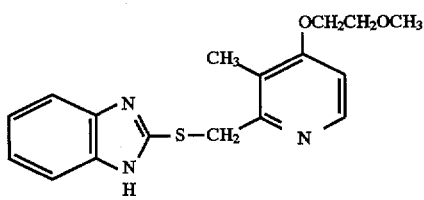

A mixture of 1.50 g of 2-mercapto-1H-benzimidazole with 2.37 g of 2-chloromethyl-4-(2-methoxy)ethoxy-3-methylpyridine, 0.51 g of sodium hydroxide (95%), and 60 ml of ethanol was stirred at 40° C. for 1.5 hr. After the completion of the addition, the reaction mixture was filtered and ethanol was distilled off from the filtrate. The residue thus obtained was purified by silica gel column chromatography (ethyl acetate/n-hexane system), thereby preparing 2.17 g of the intended product.

$^1$H-NMR (DMSO-d$_6$) δ; 2.20(s, 3H), 3.29(s, 3H), 3.55~3.74(m, 2H), 4.02~4.22(m, 2H), 4.63(s, 2H), 6.86(d, J=6.2 Hz, 1H), 6.92~7.14(m, 2H), 7.22~7.46(m, 2H), 8.13 (d, J=6.2 Hz, 1H)

Example 20

2-[{4-(2-Methoxy)ethoxy-3-methylpyridin-2-yl}methylsulfinyl]-1H-benzimidazole sodium salt

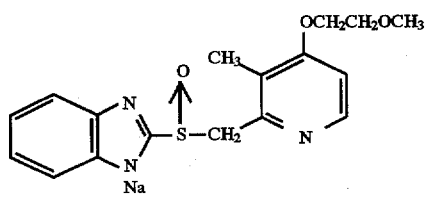

1.00 g of 2-[{4-(2-methoxy)ethoxy-3-methylpyridin-2-yl}methylthio-1H-benzimidazole was dissolved in 30 ml of dichloromethane. 0.54 g of m-chloroperbenzoic acid was added thereto at −60° C. in a nitrogen stream, followed by stirring for 0.5 hr. After the completion of the reaction, 0.5 g of triethylamine was added to the reaction mixture, and the temperature of the reaction mixture was raised to −10° C. 30 ml of an aqueous saturated sodium carbonate solution was added thereto, followed by stirring at room temperature for 0.5 hr. The dichloromethane phase was taken out and combined with an extract obtained by extraction of the water phase with 50 ml of dichloromethane, followed by drying. The dried solution was filtered and dichloromethane was distilled off from the filtrate. 0.70 g of the crystal thus obtained was weighed and dissolved in 20 ml of an aqueous 0.1N sodium hydroxide solution, followed by addition of ethanol. The resulting mixture was concentrated to dryness, washed with ether, and dried, thereby preparing 0.75 g of the intended product in the form of a crystal.

$^1$H-NMR (DMSO-d$_6$) δ; 2.16(s,3H), 3.33(s,3H), 3.60~3.76(m, 2H), 4.08~4.24(m, 2H), 4.55(ABq, J=12.5 Hz, Δv=17.3 Hz, 2H), 6.77~6.99(m, 3H), 7.37~7.56(m, 2H), 8.30(d, J=6.2 Hz, 1H)

Examples 21 to 28

The same procedures as those described above were repeated to prepare the following compounds.

(Example 21)

5-Methoxy-2-[{4-(2-methoxy)ethoxy-3-methylpyridin-2-yl}methylthio]-1H-benzimidazole

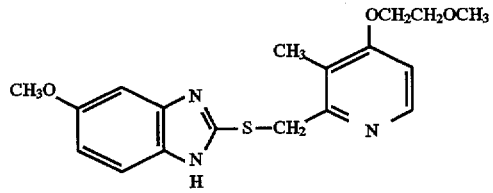

$^1$H-NMR (DMSO-d$_6$) δ; 2.22(s, 3H), 3.34(s, 3H), 3.52~3.72(m, 2H), 3.78(s, 3H), 4.04~4.26(m, 2H), 4.66(s, 2H), 6.66~7.44(m, 3H), 8.2(d,J =6.2 Hz, 1H)

(Example 22)

5-Methoxy-2-[{4-(2-Methoxy)ethoxy-3-methylpyridin-2-yl}methylsulfinyl]-1H-benzimidazole sodium salt

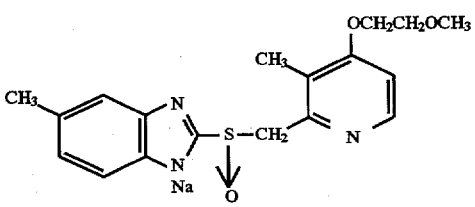

$^1$H-NMR (DMSO-d$_6$) δ; 2.28(s, 3H), 3.45(s, 3H), 3.70~3.94(m, 2H), 3.88(s, 3H), 4.20~4.47(m, 2H), 4.75 (ABq, J=13.4 Hz, Δv=19.9 Hz, 2H), 6.65~8.04(m, 3H), 8.39(d, J=6.2 Hz, 1H)

(Example 23)

2-[{4-(2-Methoxy)ethoxy-3-methylpyridin-2-yl}methylthio]-5-trifluoromethyl-1H-benzimidazole

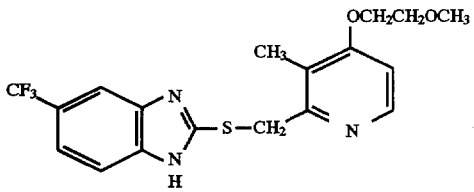

¹H-NMR (DMSO-d₆) δ; 2.27(s, 3H), 3.36(s, 3H), 3.61~3.80(m, 2H), 4.06~4.28(m 2H), 4.78(s, 2H), 6.97(d, J=5.3 Hz, 1H), 7.32~7.86(m, 3H), 8.27(d, J=5.3 Hz, 1H)

(Example 24)

2-[{4-(2-Methoxy)ethoxy-3-methylpyridin-2-yl}methylsulfinyl]-5-trifluoromethyl-1H-benzimidazole sodium salt

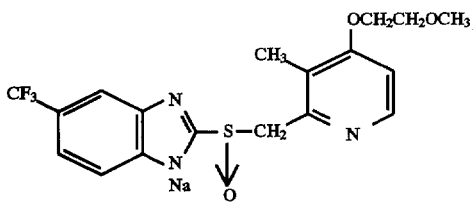

¹H-NMR (DMSO-d₆) δ; 2.17(s, 3H), 3.34(s, 3H), 3.50~3.84(m, 2H), 4.10~4.26(m, 2H), 4.65(ABq, J=12.5 Hz, Δv=16.2 Hz, 2H), 6.95(d, J=6.2 Hz, 1H), 8.18~8.96(m, 3H), 8.28(d, J=6.2 Hz, 1H)

(Example 25)

2-{4-(2-Methoxyethoxy)pyridin-2-yl}methylsulfinyl-1H-benzimidazole sodium salt

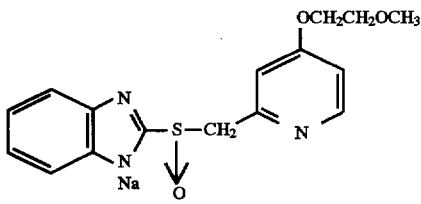

¹H-NMR (DMSO-d₆) δ; 2.26(s, 3H), 2.32(s, 3H), 3.40(s, 3H), 3.54~3.75(m, 2H), 3.84~4.04(m, 2H), 4.32(s, 2H), 6.94~7.19(m, 2H), 7.30~7.56(m, 2H), 8.16(s, 1H)

(Example 26)

2-{4-(3-Methoxyethoxy)pyridin-2-yl}methylthio-1H-benzimidazole

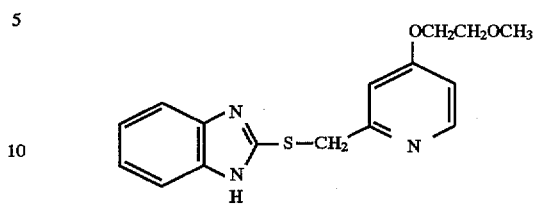

¹H-NMR (CDCl₃) δ; 3.37(s, 3H), 3.60~3.78(m, 2H), 4.00~4.18(m, 2H), 4.24(s, 2H), 6.64~6.86(m, 2H), 6.97~7.20(m, 2H), 7.32~7.58(m, 2H), 8.33(d, J=5.3 Hz, 1H)

(Example 27)

2-{4-(3-Methoxyethoxy)-3,5-dimethylpyridin-2-yl}methylsulfinyl-1H-benzimidazole sodium salt

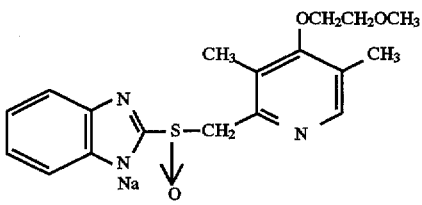

¹H-NMR (DMSO-d₆) δ; 2.16(s, 6H), 3.25(s, 3H), 3.46~3.64(m, 2H), 3.76~3.94(m, 2H), 4.47(ABq, J=12.5 Hz, Δv=19.5 Hz, 2H), 6.68~6.91(m, 2H), 7.26~7.49(m, 2H), 8.11(s, 1H)

(Example 28)

2-{4-(3-Methoxyethoxy)-3,5-dimethylpyridin-2-yl}-methylthio-1H-benzimidazole

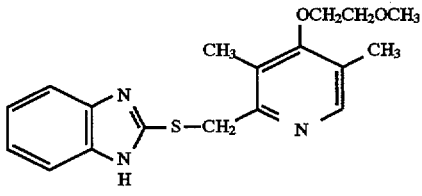

¹H-NMR (CDCl₃) δ; 3.19(s, 3H), 3.31~3.62(m, 2H), 3.72~3.99(m, 2H), 4.41(ABq, J=11.6 Hz, Δv=11.0 Hz, 2H) 6.56~6.96(m, 4H), 7.28~7.51(m, 2H), 8.44(d, J=6.2 Hz, 1H)

We claim:

1. A compound of the formula:

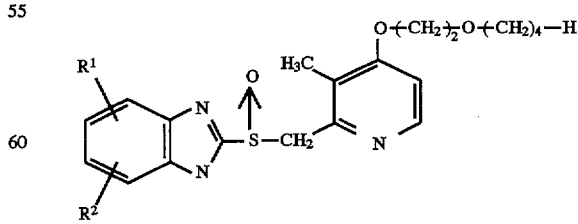

wherein $R^1$ and $R^2$ are independently hydrogen, lower alkyl, lower alkoxy, halogen, or halogenated lower alkyl, and the pharmaceutically acceptable salt thereof.

2. A compound as claimed in claim 1 wherein $R^1$ is methoxy and $R^2$ is hydrogen.

3. A compound as claimed in claim 1 wherein $R^1$ and $R^2$ are both hydrogen.

4. A compound as claimed in claim 1 wherein $R^1$ is $CF_3$ and $R^2$ is hydrogen.

5. A compound as claimed in claim 1 wherein $R^1$ is methyl and $R^2$ is hydrogen.

6. A compound as claimed in claim 1 wherein $R^1$ is chlorine and $R^2$ is hydrogen.

7. A compound selected from the group consisting of:

2-[4-{(2-butoxy)ethoxy}-3-methylpyridin-2-yl] methylsulfinyl-5-methoxy-1H-benzimidazole;

2-[4-{(2-butoxy)ethoxy}-3-methylpyridin-2-yl] methylsulfinyl-5-trifluoromethyl-1H-benzimidazole;

2-[4-{(2-butoxy)ethoxy}-3-methylpyridin-2-yl] methylsulfinyl-5,6-dimethyl-1H-benzimidazole, and 2-[4-{(2-butoxy)ethoxy}-3-methylpyridin-2-yl] methylsulfinyl-5-chloro-1H-benzimidazole.

8. A pharmaceutical composition comprising together with a pharmaceutically acceptable carrier an effective amount of a compound of the formula:

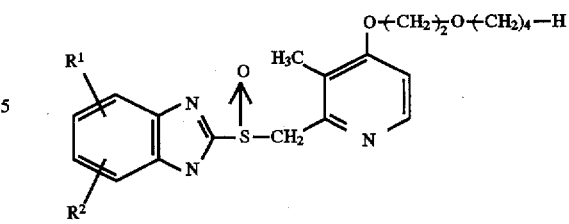

wherein R1 and R2 are independently hydrogen, lower alkyl, lower alkoxy, halogen or, halogenated lower alkyl, and the pharmaceutically acceptable salt thereof.

9. A method of treating peptic ulcers comprising administering to a person suffering therefrom an effective amount of a compound of the formula:

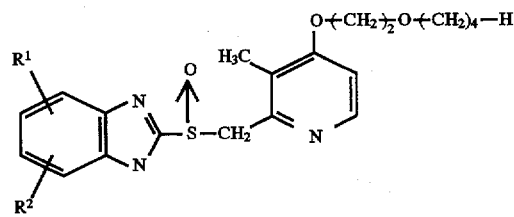

wherein $R^1$ and $R^2$ are independently hydrogen, lower alkyl, lower alkoxy, halogen or halogenated lower alkyl, and the pharmaceutically acceptable salt thereof.

* * * * *